US00PP25412P2

(12) United States Plant Patent
Hill et al.

(10) Patent No.: US PP25,412 P2
(45) Date of Patent: Apr. 7, 2015

(54) ***HYDRANGEA* PLANT NAMED 'DOUGHILL'**

(50) Latin Name: *Hydrangea quercifolia*
Varietal Denomination: Doughill

(71) Applicants: Doug Hill, Cleveland, AL (US); Brenda Hill, Cleveland, AL (US)

(72) Inventors: Doug Hill, Cleveland, AL (US); Brenda Hill, Cleveland, AL (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,723

(22) Filed: Aug. 23, 2013

(51) Int. Cl.
*A01H 5/00* (2006.01)

(52) U.S. Cl.
USPC ..... Plt./250

(58) Field of Classification Search
USPC ..... Plt./250
See application file for complete search history.

(56) References Cited

PUBLICATIONS

UPOV Hit for Doughill, PLUTO: Plant Variety Database, publication date Oct. 31, 2012.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'Doughill', characterized by its upright and outwardly spreading plant habit; vigorous growth habit; strong and sturdy stems; and large inflorescences with light green to white-colored double-type flowers

3 Drawing Sheets

Botanical designation: *Hydrangea quercifolia.*
Cultivar denomination: 'DOUGHILL'.

BACKGROUND OF THE INVENTION

The present invention relates to a new and distinct *Hydrangea* plant, botanically known as *Hydrangea quercifolia* and hereinafter referred to by the name 'Doughill'.

The new *Hydrangea* plant is a product of a planned breeding program conducted by the Inventors in Cleveland, Ala. The objective of the breeding program was to develop new *Hydrangea* plants with interesting inflorescence forms.

The new *Hydrangea* plant originated from an open-pollination in 1988 of an unnamed seedling selection of *Hydrangea quercifolia*, not patented, as the female, or seed parent with an unknown selection of *Hydrangea quercifolia* as the male, or pollen, parent. The new *Hydrangea* plant was discovered and selected by the Inventors as a single flowering plant from within the progeny of the stated open-pollination in a controlled environment in Cleveland, Ala. in 1990.

Asexual reproduction of the new *Hydrangea* plant by softwood cuttings in a controlled environment in Cleveland, Ala. since July, 2004 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Doughill'.

These characteristics in combination distinguish 'Doughill' as a new and distinct *Hydrangea* plant:

1. Upright and outwardly spreading plant habit.
2. Vigorous growth habit.
3. Strong and sturdy stems.
4. Large inflorescences with light green to white-colored double-type flowers.

Plants of the new *Hydrangea* differ from plants of the female parent selection in the following characteristics:

1. Inflorescences of plants of the new *Hydrangea* are denser with more flowers than inflorescences of plants of the female parent selection.
2. Plants of the new *Hydrangea* have double-type sterile flowers whereas plants of the female parent selection have single-type sterile flowers.
3. Sepals of sterile flowers of plants of the new *Hydrangea* are deltoid in shape with acute apices whereas sepals of sterile flowers of plants of the female parent selection are rounded to oblong in shape with broadly obtuse to rounded apices.

Plants of the new *Hydrangea* can be compared to plants of *Hydrangea quercifolia* 'Snowflake', not patented. In side-by-side comparisons, plants of the new *Hydrangea* differed primarily from plants of 'Snowflake' in sepal shape as sepals of sterile flowers of plants of the new *Hydrangea* were deltoid in shape with acute apices whereas sepals of sterile flowers of plants of 'Snowflake' were oblong in shape with obtuse apices.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a top perspective view of a typical flowering plant of 'Doughill' grown in an outdoor nursery.

The photographs on the second and third sheets are close-up views of typical inflorescences 'Doughill'.

DETAILED BOTANICAL DESCRIPTION

Plants used for the aforementioned photographs and the following description were grown during the summer in the ground and in three-gallon containers in an outdoor nursery in Grand Haven, Mich. and under cultural practices typical of commercial *Hydrangea* production. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea quercifolia* 'Doughill'.

Parentage:

*Female, or seed, parent*.—Unnamed seedling selection of *Hydrangea quercifolia*, not patented.

*Male, or pollen, parent*.—Unknown selection of *Hydrangea quercifolia*, not patented.

Propagation:

*Type cutting*.—By softwood cuttings.

*Time to initiate roots, summer*.—About 28 days at temperatures of about 24° C.

*Time to produce a rooted young plant, summer*.—About four months at temperatures of about 24° C.

*Root description*.—Fine, fibrous; white in color.

*Rooting habit*.—Freely branching; dense.

Plant description:

*Plant form and growth habit*.—Perennial deciduous shrub; upright and outwardly spreading plant habit; broad inverted triangle; strong and sturdy lateral branches; freely branching habit with about six lateral branches per plant; vigorous growth habit.

*Plant height*.—About 52 cm.

*Plant diameter or area of spread*.—About 59 cm.

*Lateral branches*.—Length: About 41 cm. Diameter: About 5 mm. Internode length: About 4.5 cm. Texture: Smooth, glabrous. Strength: Strong, sturdy. Color: Close to 166C; with development becoming closer to 176A.

Leaf description:

*Arrangement*.—Opposite, simple.

*Length*.—About 11.5 cm.

*Width*.—About 10.5 cm.

*Shape*.—Ovate.

*Apex*.—Acuminate.

*Base*.—Obtuse.

*Margin*.—Palmately lobed; serrulate.

*Texture, upper surface*.—Pubescent.

*Texture, lower surface*.—Coarse; pubescent.

*Venation pattern*.—Palmate.

*Color*.—Developing leaves, upper surface: Close to 144A. Developing leaves, lower surface: Close to 147C. Fully expanded leaves, upper surface: Close to 146A; venation, close to 139A. Fully expanded leaves, lower surface: Close to 147C; venation, close to 152C.

*Petioles*.—Length: About 3.5 cm. Diameter: About 3 mm. Texture, upper and lower surfaces: Pubescent. Color, upper surface: Close to 166D. Color, lower surface: Close to 146C.

Flower description:

*Flower type and habit*.—Single sterile and fertile flowers arranged on large terminal mophead-type panicles; flowers face upright or outwardly.

*Fragrance*.—Moderately fragrant; pleasant.

*Natural flowering season*.—Plants flower continuously throughout the summer in Grand Haven, Mich.

*Quantity of flowers*.—Freely flowering habit; about 189 fertile flowers and about 29 double-type sterile flowers per inflorescence.

*Inflorescence height*.—About 11 cm.

*Inflorescence diameter*.—About 10 cm.

*Flower diameter, fertile flowers*.—About 5 mm.

*Flower depth (height), fertile flowers*.—About 3 mm.

*Flower diameter, sterile flowers*.—About 2.6 cm.

*Flower depth (height), sterile flowers*.—About 1.2 cm.

*Flower buds, fertile flowers*.—Length: About 1 mm. Diameter: About 1 mm. Shape: Obovate. Color: Close to 144C.

*Flower buds, sterile flowers*.—Length: About 2 mm. Diameter: About 1 mm. Shape: Obovate. Color: Close to 145B.

*Petals, fertile flowers only*.—Arrangement: Five in a single whorl. Length: About 2 mm. Width: About 1 mm. Shape: Elliptic. Apex: Acute. Base: Cuneate. Margin: Entire. Texture, upper and lower surfaces: Smooth, glabrous. Color: When opening, upper and lower surfaces: Close to 151D. Fully opened, upper and lower surfaces: Close to 3D.

*Sepals, fertile flowers*.—Quantity per flower: Five in a single whorl. Length: About 0.5 mm. Width: About 0.5 mm. Shape: Subulate. Apex: Acute. Base: Cuneate. Margin: Entire. Texture, upper and lower surfaces: Smooth, glabrous. Color: When opening, upper and lower surfaces: Close to 145D. Fully opened, upper and lower surfaces: Close to 145D.

*Sepals, sterile flowers*.—Quantity per flower: Sixteen in a several whorl. Length: About 1.3 cm. Width: About 7 mm. Shape: Roughly deltoid. Apex: Acute. Base: Cuneate. Margin: Entire. Texture, upper and lower surfaces: Smooth, glabrous. Color: When opening, upper and lower surfaces: Close to 157B tinged with light green. Fully opened, upper surface: Close to 157B. Fully opened, lower surface: Close to 157D.

*Pedicels, fertile flowers*.—Angle: About 80° to 95° from inflorescence axis. Strength: Strong, sturdy. Length: About 8 mm. Diameter: About 1 mm. Texture: Smooth. Color: Close to 145C.

*Pedicels, sterile flowers*.—Angle: About 40° to 50° from inflorescence axis. Strength: Moderately strong. Length: About 1.2 cm. Diameter: About 1 mm. Texture: Smooth. Color: Close to 145A.

*Reproductive organs, fertile flowers only*.—Stamens: Quantity per flower: About seven. Filament length: About 2 mm. Filament color: Close to 145C. Anther shape: Round. Anther length: About 1 mm. Anther color: Close to 155B. Pollen amount: None observed. Pistils: Pistil quantity per flower: About three. Pistil length: About 5 mm. Stigma shape: Round. Stigma color: Close to 145C. Style length: About 1 mm. Style color: Close to 145C. Ovary color: Close to 145B.

*Seeds*.—Quantity per inflorescence: Numerous. Size: Less than 0.1 mm by less than 0.1 mm. Color: Brown.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures ranging from about −16° C. to about 44° C.

It is claimed:

1. A new and distinct *Hydrangea* plant named 'Doughill' as illustrated and described.

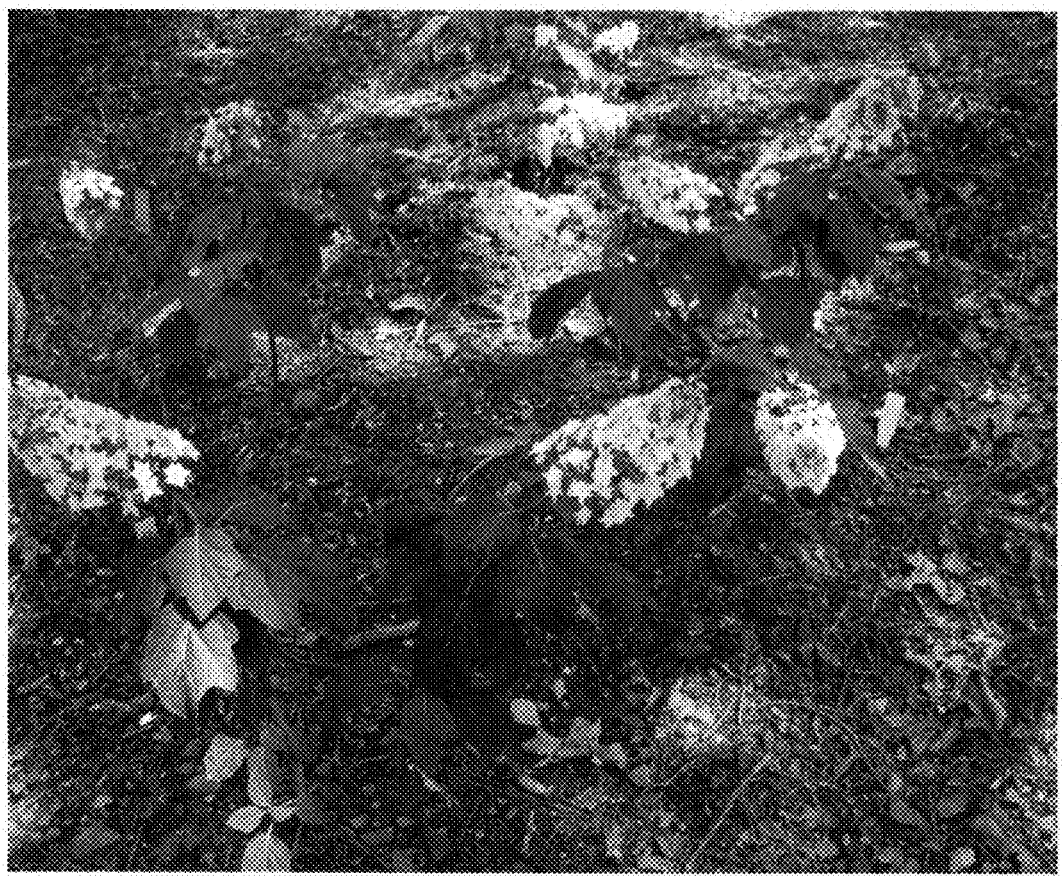

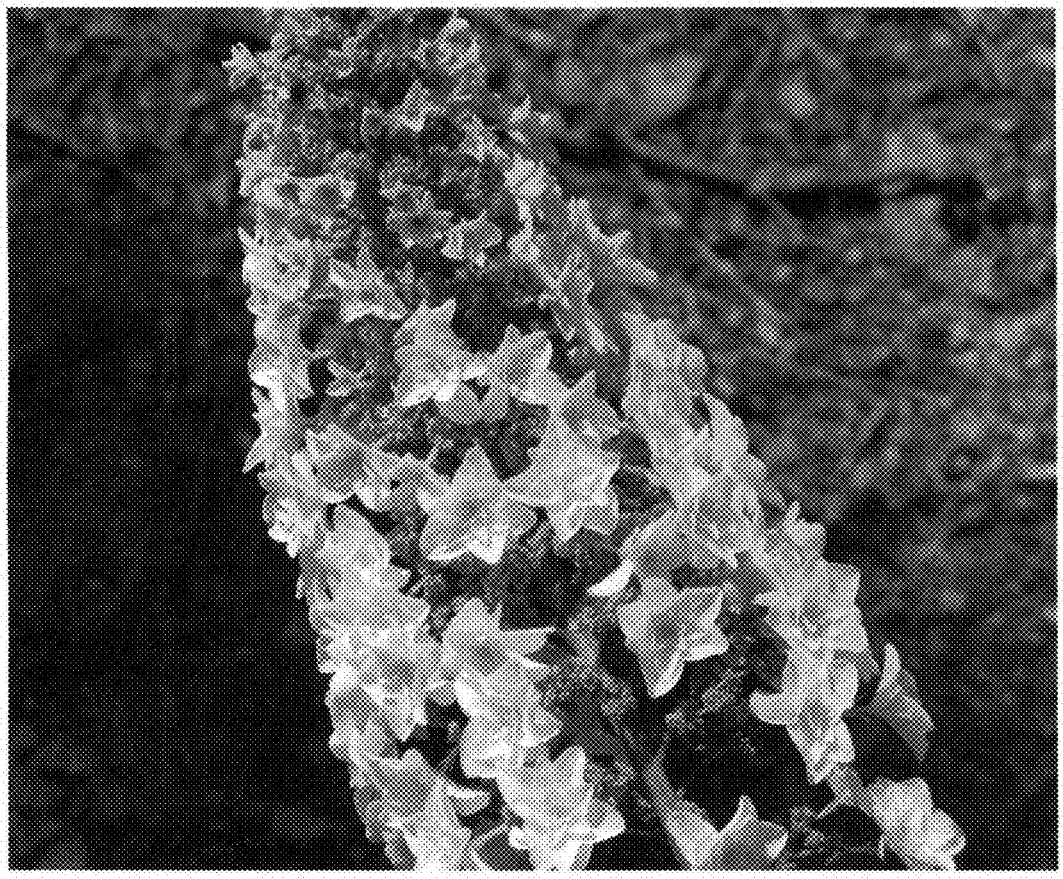

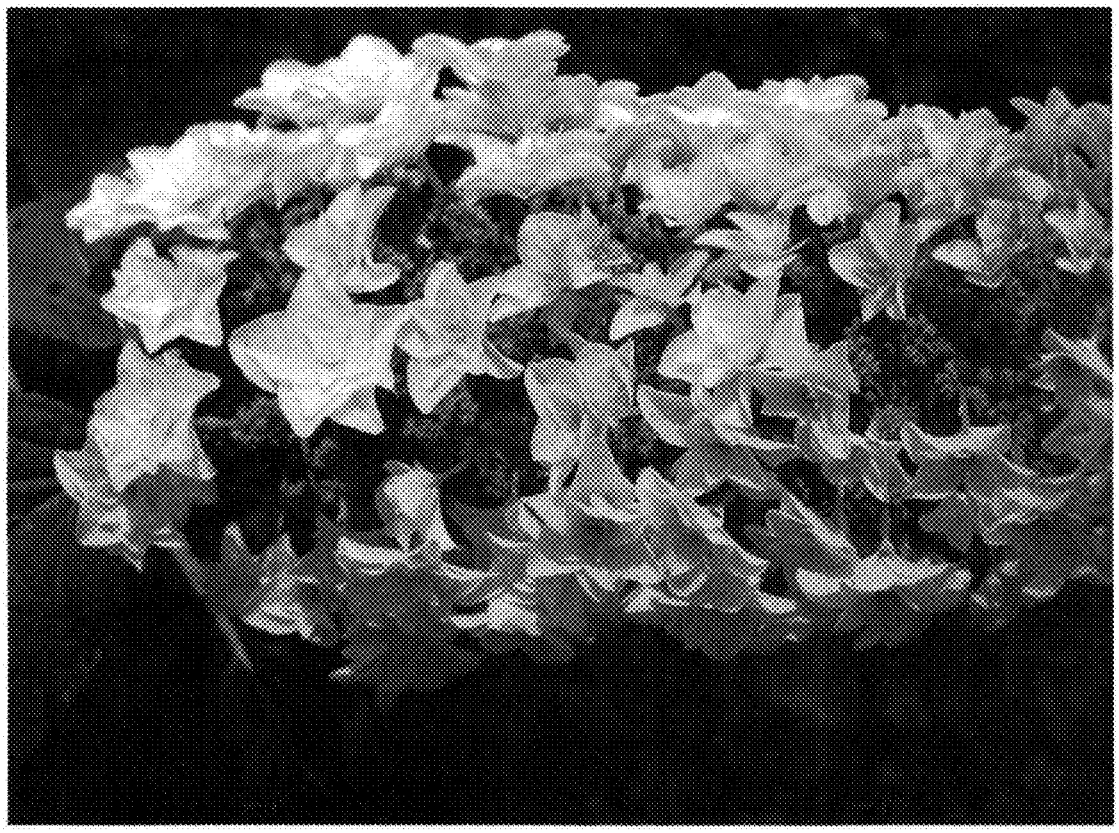

* * * * *